United States Patent [19]

Kretz

[11] 4,416,989

[45] Nov. 22, 1983

[54] METHOD OF CONTINUOUS TREATMENT OF GRAIN MASH FOR PRODUCING ETHANOL

[75] Inventor: Rolf H. Kretz, Singen, Fed. Rep. of Germany

[73] Assignee: Process Engineering Company S.A., Maennedorf, Switzerland

[21] Appl. No.: 321,897

[22] Filed: Nov. 16, 1981

[30] Foreign Application Priority Data

Nov. 25, 1980 [CH] Switzerland ...................... 8684/80

[51] Int. Cl.³ ........................... C12C 7/04; C12P 7/06
[52] U.S. Cl. ........................................ 435/93; 426/11; 426/29; 426/495; 426/518; 435/161
[58] Field of Search ..................... 426/11, 16, 29, 495, 426/518; 435/93, 161

[56] References Cited

U.S. PATENT DOCUMENTS

| | | | |
|---|---|---|---|
| 2,894,841 | 7/1959 | Compton et al. | 426/495 X |
| 3,989,848 | 11/1976 | Moll et al. | 435/93 X |
| 4,092,434 | 5/1978 | Yoshizumi et al. | 426/29 X |
| 4,207,345 | 6/1980 | Van Ghelume et al. | 426/29 X |

OTHER PUBLICATIONS

Rose, A. H., Alcoholic Beverages Economic Microbiology, vol. 1, Academic Press, N.Y., 1977, (pp. 71–74).

*Primary Examiner*—David M. Naff
*Attorney, Agent, or Firm*—Michael J. Striker

[57] ABSTRACT

A method of continuous treatment of grain mash for production of ethanol includes enzymatic liquefying of starch-containing particles of raw material in a liquefying container, separating not decomposed coarser particles of raw material in the container, withdrawing the coarse particles of raw material from the container and comminuting the same, and recirculating the comminuted particles of raw material into the container. The starch-containing particles are not ground very fine such as to pass through 1-3 mm diameter sieve openings, and coarse particles withdrawn from the container are comminuted to a fine particle size preferably with a wet comminuting device. By this method, fine particles are obtained with low energy consumption.

10 Claims, 1 Drawing Figure

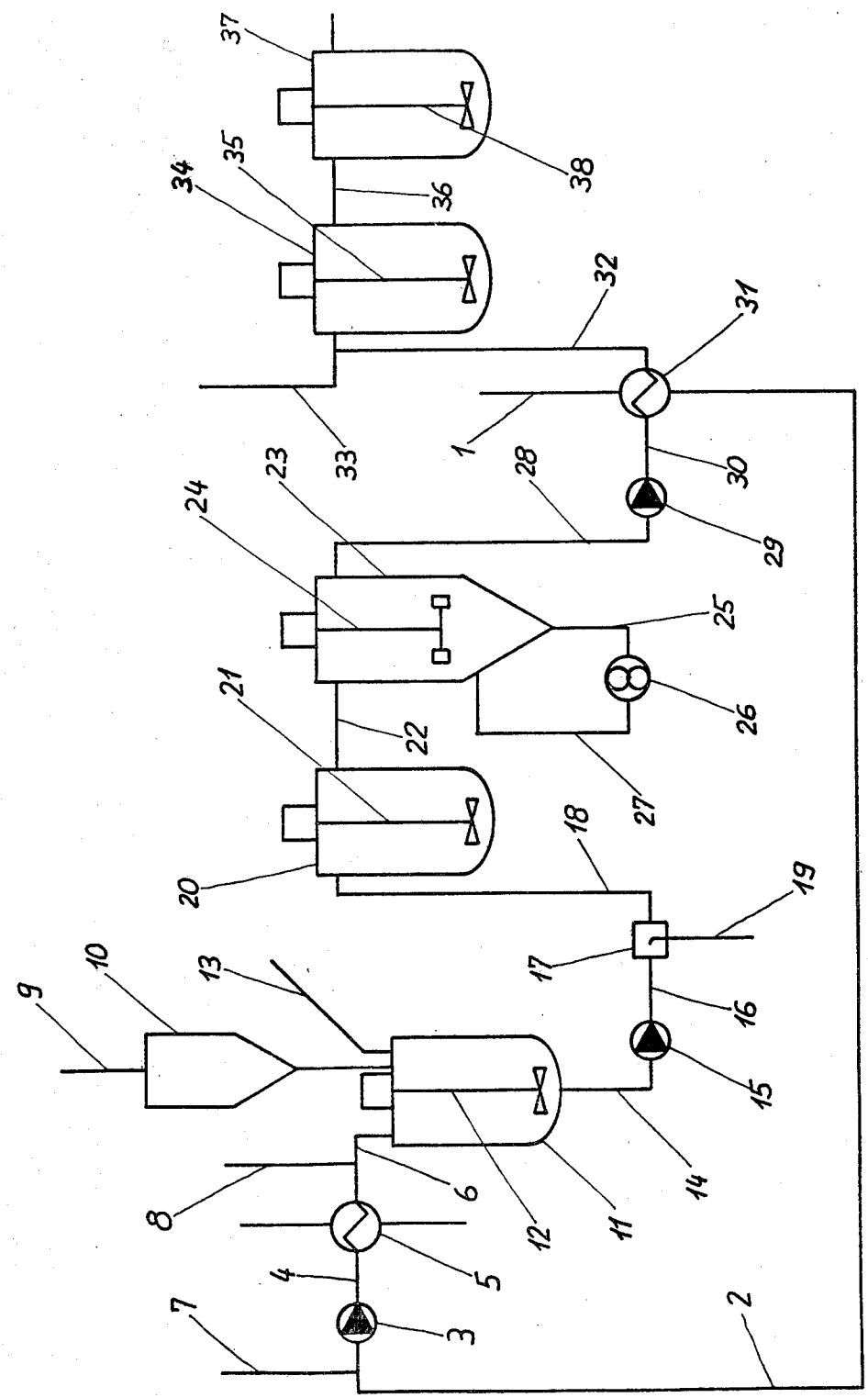

METHOD OF CONTINUOUS TREATMENT OF GRAIN MASH FOR PRODUCING ETHANOL

BACKGROUND OF THE INVENTION

The present invention relates to a method of continuous treatment of grain mash with low temperatures for production of ethanol, wherein enzymes are introduced in two steps for decomposition of the starch to glucose.

For continuous treatment of mash with enzymes, it is necessary to divide the raw material very finely so that the material can be effectively utilized. In the event that the raw material is comminuted coarsely, the enzymatic decomposition cannot be performed sufficiently fast and completely. On the other hand, too fine a grinding is not desirable, on energy considerations. A method of two-step enzymatic production of dextrose is disclosed in German Offenlegungsschrift No. 2,618,131, wherein a wet grinding of a homogeneous suspension of coarse and fine particles is performed in a cycle. In this method, contrary to the present invention, the small particles are again broken into pieces, which does not provide for any advantage inasmuch as it requires high energy consumption.

Another two-step enzyme process is known from U.S. Pat. No. 4,092,434, in which alcohol is produced from grain, wherein the starch is liquefied with addition of alpha-amylase in condition of 75°–85° C. After cooling to 25°–35° C., the beta-glucosidase is added for saccharifying.

In all known continuous low-temperature processes, the grain is mixed in a mixer with 2–3 times water quantity, heated by direct vapor to 60°–90° C., mixed with alpha-amylase and pumped through a contact delay tank or a pipe system. After adjusting the temperature and the pH-value, the amyloglucosidase is added, and the further reaction takes place either in a second contact delay system, or the mash is cooled and pumped directly to a fermentor.

Low-temperature mash processes operate economically because of reduced vapor consumption as compared with the high-temperature processes. The entire energy consumption is, however, not entirely favorable when the costs for the comminution of the grain are taken into consideration. The material must be ground to flour fineness, because otherwise the yield is unsatisfactory. Price-favorable comminution of dried grain is performed in a hammer mill or a wing beater mill. In both systems, the classification is carried out by a built-in sieve insert with opening diameters of 2 mm. The smaller the particles of the starch-containing material, the more complete is the enzymatic decomposition of the starch-containing material particles. On the other hand, it is not meaningful to communite the material to such an extent that all particles exceed a predetermined high limit, for example 0.3 mm, inasmuch as then the natural part of the particles are considerably smaller than required in accordance with the process. The energy and instrument costs increase exponentially with fine grinding and lump-free mixing in water is expensive. A compromise between grinding expenditures and grain size didtribution must be achieved.

SUMMARY OF THE INVENTION

Accordingly, it is an object of the present invention to provide a method of continuous treatment of grain mash for production of ethanol, which avoids the disadvantages of the prior art.

More particularly, it is an object of the present invention to provide a method of continuous treatment of grain mash for production of ethanol, which in condition of low energy consumption provides for the greatest possible saccharification grade.

In keeping with these objects and with others which will become apparent hereinafter, one feature of the present invention resides, briefly stated, in a method for the continuous treatment of grain mash for production of ethanol, which includes enzymatic liquefying of starch-containing particles of raw material in a liquefying container, wherein not decomposed coarse particles of raw material are separated and withdrawn from the container whereupon the thus withdrawn coarse particles are comminuted and recirculated into the container.

With the method according to the present invention, the starch-containing material to be treated must not be ground very fine, whereas for example, it may be ground with a sieve insert having opening diameters of 3 mm instead of 2 mm. In addition, only not decomposed greater particles to a certain method parameter are comminuted. Since these particles to this time point have been already softened, they can be broken very easily and with low energy consumption.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE of the drawing is a schematic view illustrating a method of continuous treatment of grain mash for producing ethanol, in accordance with the present invention.

DESCRIPTION OF A PREFERRED EMBODIMENT

A mash water preheated in a heat exchanger 31 is supplied by a pump 3 via a conduit 4 to a heat exchanger 5 and via a conduit 6 to a mixing container 11. Other liquids such as slop or yeast wash water can be supplied in dosed quantities via conduits 7 and 8. Grain is supplied from a not shown silo via a conduit 9 and is comminuted in a mill or grinder 10. Thereupon it is supplied to a mixing container 11 in which it is subjected to an intensive mixing by a stirrer 12. The ratio of the mash water to grain lies within the range between 2:1 and 3:1. The temperature attained in the operation of the mixing container 11 lies within 60°–70° C. The mash water must, in the event of a mixture ratio of 2 parts of water to 1 part of grain to be comminuted, have a temperature of 70°–98° C. The mixing container 11 is continuously supplied by a not shown dosing pump via a conduit 13, with a suitable alpha-amylase preparation.

A certain quantity of the mixture corresponding to the supply is fed by a pump 15 to a vapor injector 17 in which the material is further heated, for example to 60°–85° C., if the required temperature has not been attained. Via a conduit 18, the mash flows to a multi-stage contact delay system which, for example, includes a container 20, a stirring member 21, a transfer conduit 22, a container 23, and stirring member 24. The container 23 is so designed that heavier particles are settled in a conical part of the container, which is reinforced by a slow rotation of the stirring member 24 with less than 30 revolutions per minute. The stirring is performed in the cylindrical part of the container 23. The settled material together with the liquid is supplied via a conduit 25 to mill or grinder 26. It is comminuted there to a particle size adjustable in the mill and supplied back via a conduit 27 to the container 23. The comminuted particles of the raw material are in a preferable manner introduced tangentially into the upper region of the conical portion of the container 23. The mill is, for example, a pinned disk mill with adjustable grinding gap. This mill type and similar in-line wet comminution systems have a pumping action so that no additional pump is required.

The mash exits the container 23 via a conduit 28 and flows either directly or via a not shown further contact delay container to a pump 29 and to the heat exchanger 31. Through a conduit 32, flows the mash, after addition of amyloglucosidase-containing enzyme preparations, to a saccharification line which includes, for example, two containers 34 and 37 with stirring members 35 and 38. After passing through these containers, the mash is cooled in a not shown heat exchanger and conveyed to fermentation apparatus.

By the comminution of the particles after the liquefication, the portion of fermentatable sugar, and thereby the alcohol yield, is considerably increased, and thereby the efficiency of the method is improved.

Instead of the sedimentation container, a decanter centrifuge can be utilized for acceleration of the separation of the raw material particles.

The grain mash utilized in the process can be a material comminuted in a comminuting device with sieve openings of 1-3 mm diameter, wherein the comminuting device may be a hammer drill or a wing beater mill.

It will be understood that each of the elements described above, or two or more together, may also find a useful application in other types of methods differing from the types described above.

While the invention has been illustrated and described as embodied in a method of continuous treatment of grain mash for producing ethanol, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A method of producing grain mash for producing ethanol, comprising the steps of comminuting a starch-containing raw material in a comminuting device with sieve openings of about 1-3 mm diameter to produce particles of the starch-containing raw material, enzymatic liquefying the starch-containing particles of raw material in a liquefying container in the form of a sedimentation container, continuously separating non-decomposed coarser ones of the particles of raw material in the container, continuously withdrawing the separated coarser particles of raw material from the container, continuously comminuting the withdrawn coarse particles in a wet comminuting device to a substantially smaller particle size, and continuously recirculating the smaller particles of raw material from the wet comminuting device into the liquefying container.

2. A method defined in claim 1, wherein the container has a bottom, said withdrawing step includes withdrawing the coarser particles of raw material from the bottom of the container.

3. A method defined in claim 1, wherein said liquefying step includes forming a suspension of the particles of raw material; and further comprising the step of moving the suspension in the container with less than 30 revolutions per minute of a stirring member.

4. A method defined in claim 3, wherein the container has a cylindrical portion, said moving step including moving the suspension in the cylindrical portion of the container.

5. A method defined in claim 1, wherein said container has a conical portion with an upper region, said recirculating step includes introducing tangentially the comminuted particles of raw material into the upper region of the conical portion of the container.

6. A method defined in claim 1, wherein said liquefying step includes supplying liquefying enzymes; and further comprising the step of heating the mash to 70°-90° C. before said supplying step.

7. A method defined in claim 1; and further comprising the step of preheating a mash water with surplus heat produced in a heat exchanger and introducing the mash water into the container.

8. A method defined in claim 7; and further comprising the step of further heating the preheated mash water to 70°-98° C. in a further heat exchanger.

9. A method defined in claim 1, wherein said comminuting device is a hammer mill.

10. A method defined in claim 1, wherein said comminuting device is a wing beater mill.

* * * * *